(12) United States Patent
De Kraker et al.

(10) Patent No.: US 7,094,922 B2
(45) Date of Patent: Aug. 22, 2006

(54) PROCESS FOR PRODUCTION OF ESSENTIALLY CHLORIDE-FREE CALCIUM SULFONATE

(75) Inventors: Abraham Robert De Kraker, Sugar Land, TX (US); Steven Allen Holmes, Houston, TX (US); Krishna Rangraj Kaushik, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/824,785

(22) Filed: Apr. 15, 2004

(65) Prior Publication Data
US 2005/0004392 A1    Jan. 6, 2005

Related U.S. Application Data

(63) Continuation-in-part of application No. 10/417,788, filed on Apr. 17, 2003, now abandoned.

(51) Int. Cl.
*C07C 309/00*    (2006.01)
(52) U.S. Cl. ....................................................... 562/33
(58) Field of Classification Search .................... None
See application file for complete search history.

(56) References Cited

U.S. PATENT DOCUMENTS

| | | | |
|---|---|---|---|
| 2,266,325 A | 12/1941 | Lazar et al. | 252/33 |
| 2,402,325 A | 6/1946 | Griesinger et al. | 252/33 |
| 2,418,894 A | 4/1947 | McNab et al. | 252/33 |
| 2,779,784 A | 1/1957 | Sharrah | 260/505 |
| 2,846,466 A | 8/1958 | Crosby et al. | 260/504 |
| 2,884,445 A | 4/1959 | Axe et al. | 260/504 |
| 2,909,563 A | 10/1959 | Whitney | 260/504 |
| 2,915,517 A | 12/1959 | Le Suer | 260/139 |
| 3,007,868 A | 11/1961 | Eck et al. | 252/33 |
| 3,023,231 A | 2/1962 | Logan | 260/504 |
| 3,260,670 A | 7/1966 | Richardson | 252/33 |
| 3,719,596 A | 3/1973 | Shore et al. | 252/1 |
| 4,279,837 A | 7/1981 | Wellbrock | 260/505 N |
| 4,615,841 A | 10/1986 | Stamatakis et al. | 260/505 N |
| 5,578,235 A | 11/1996 | Jao et al. | 508/391 |
| 5,789,615 A | 8/1998 | Alcock et al. | 562/97 |
| 5,804,094 A | 9/1998 | Alcock et al. | 252/18 |

FOREIGN PATENT DOCUMENTS

| | | |
|---|---|---|
| GB | 709587 | 1/1952 |
| GB | 1172779 | 8/1967 |
| GB | 1179868 | 10/1967 |
| KR | 9104672 | 7/1991 |
| SU | 1002287 | 3/1983 |
| SU | 1002288 | 6/1983 |

*Primary Examiner*—Paul A. Zucker

(57) ABSTRACT

The invention relates to a process for the preparation of a low-base number calcium sulfonate that is essentially chloride free. The process involves preparing a sulfonic acid solution by adding a solvent to a sulfonic acid, optionally removing dissolved or entrained $SO_2$ or $SO_3$, mixing the solution with a specific amount of water and calcium hydroxide, heating the mixture, separating out excess calcium hydroxide from the mixture, removing the solvent and recovering the calcium sulfonate product in oil.

27 Claims, 3 Drawing Sheets

PROCESS FOR PRODUCTION OF ESSENTIALLY CHLORIDE-FREE CALCIUM SULFONATE

This patent application is a continuation-in-part of U.S. patent application Ser. No. 10/417,788 filed on Apr. 17, 2003, now abandoned the entire disclosure of which is hereby incorporated by reference.

FIELD OF THE INVENTION

The invention relates to a process for the production of low base number essentially chloride-free calcium sulfonate.

BACKGROUND OF THE INVENTION

Low base number calcium sulfonates are generally produced by the reaction of sulfonic acid with calcium hydroxide or calcium oxide, utilizing a promoter such as an alkanol. They can also be produced from sodium sulfonate by the use of calcium hydroxide or oxide and calcium chloride. Such sulfonates may be used as highly valued additives for lubricating oils such as passenger car, diesel, and marine engine lubricants. They may be further processed into overbased sulfonates, which have higher base numbers and are also used as additives for specialty lubricating oils.

When calcium sulfonate is derived from sulfonic acid, no chloride is needed, but the concentration of the final product is limited by the concentration of the sulfonic acid. In the case of natural petroleum sulfonic acid, concentration is typically less than commercially desired. Concentrating sulfonic acid itself is difficult due to its high corrosivity.

When calcium sulfonate is made from sodium sulfonate, chloride is required to make the reaction proceed. This leads to residual contaminating chloride in the final product. The sodium sulfonate is concentrated to the required concentration using a solvent extraction process prior to conversion to the calcium product, since calcium sulfonate is more difficult to concentrate by this method.

A number of methods have been disclosed for the production of low base number calcium sulfonate.

U.S. Pat. No. 5,804,094 teaches a method of producing a low base number calcium sulfonate of greater than 500 molecular weight using carboxylic acid and a high base number calcium sulfonate.

U.S. Pat. No. 5,789,615 teaches the use of staged addition of calcium hydroxide to sulfonic acid to produce a low viscosity, low haze product without the use of promoters, especially without the use of chloride. The calcium hydroxide is added in two or more steps, with 30–180 minutes heat soak after each step.

U.S. Pat. No. 4,615,841 describes a method of producing calcium sulfonates in the presence of an alkanol.

U.S. Pat. No. 4,279,837 teaches the preparation of alkaline earth metal salts of alkyl benzene sulfonic acids by neutralization of the acid using an oxyalkylate as a promoter, thus also producing a chloride free calcium sulfonate.

U.S. Pat. No. 3,719,596 describes a method of producing calcium sulfonate in which the reaction mixture is made acidic and then basic again using an alkanolamine.

U.S. Pat. No. 2,779,784 teaches a method of producing calcium sulfonate in which sulfonic acid is neutralized with calcium hydroxide at 220° F. to 390° F. (104° C. to 199° C.), in the presence of ½ to 10 parts water per part calcium hydroxide. This would correspond to between 0.12 and 2.4 mol water per mol calcium hydroxide.

It would be advantageous to produce low base number calcium sulfonates, that are free of residual chlorine and easily concentrated, via a process suitable for use in a continuous reactor that can also produce products with a low viscosity.

SUMMARY OF THE INVENTION

A method has been discovered to produce low base number calcium sulfonate, which is essentially free of residual chlorine and easily concentrated. The method can also produce a low viscosity product. The method may also be practiced in a continuous manner.

Accordingly the present invention provides a process for the production of low base number calcium sulfonates comprising:
  a. preparing a sulfonic acid-oil solution by adding about 1 to about 20 volumes of a miscible solvent to a sulfonic acid-oil feedstock and optionally removing dissolved or entrained $SO_2$ or $SO_3$ if present;
  b. mixing the sulfonic acid-oil solution with about 1 to about 5 moles of water per mol of sulfonic acid and about 1 to about 10 moles of calcium hydroxide per mole of sulfonic acid to provide a reaction mixture;
  c. heating the reaction mixture to a temperature in the range of about 40° C. to about 200° C.;
  d. separating excess calcium hydroxide from the heated-reaction mixture to produce a reaction product comprising solvent, oil, and calcium sulfonate;
  e. removing the solvent from the reaction product to produce an intermediate product comprising oil and calcium sulfonate;
  f. optionally concentrating the intermediate product by removing at least a portion of the oil to produce a concentrated product; and
  g. recovering the intermediate product and/or concentrated product, wherein the product is essentially chloride free calcium sulfonate in oil.

DETAILED DESCRIPTION OF THE INVENTION

Figure 1:
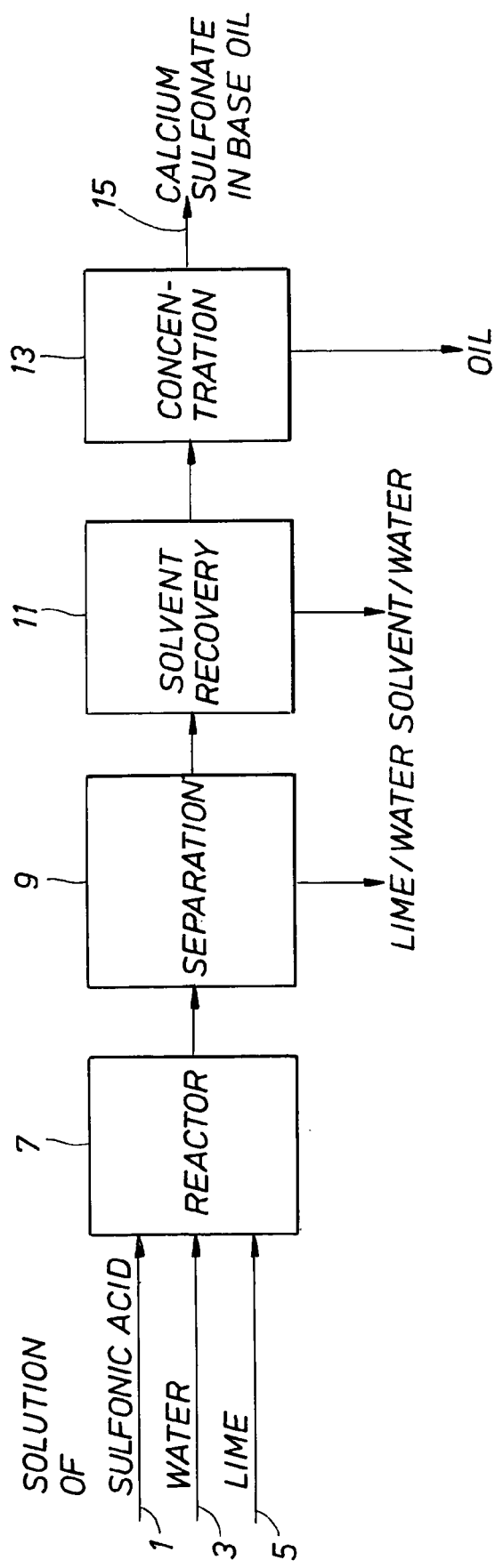
FIG. 1—This figure shows a flow chart of a continuous process for producing calcium sulfonate.

The present invention provides a process for the production of low base number essentially chloride-free calcium sulfonate. In the context of the instant application, a low base number calcium sulfonate has a base number of 0 to about 50. By "essentially chloride-free" is meant a maximum chlorine content of 1000 ppm. In a particular embodiment, the present invention provides a process for the production of calcium sulfonate which comprises preparing sulfonic acid solution by adding about 1 to about 20 volumes of a miscible solvent to sulfonic acid and removing dissolved or entrained $SO_2$ or $SO_3$ if present, mixing the resultant sulfonic acid solution with about 1 to about 5 moles of water per mol of sulfonic acid and about 1 to about 10 moles of calcium hydroxide per mole of sulfonic acid to prepare a reaction mixture, heating the reaction mixture to between about 40° C. and about 200° C. for a period of time up to about 60 minutes with stirring, separating excess calcium hydroxide and calcium salts of mineral acid from such a reaction mixture, and recovering solvent and oil to make an essentially chloride-free calcium sulfonate product.

Sulfonic acid in an oil/solvent solution or dispersion is neutralized by calcium hydroxide in the presence of a specific amount of water. Excess hydroxide and inorganic salt if any are subsequently removed from the reaction mixture by a suitable means such as centrifugation or filtration before removal of the solvent. In one embodiment, after removal of the solvent, the calcium sulfonate in oil may be concentrated by suitable means such as vacuum flashing or vacuum distillation, to produce a final product with a base number between 0 and about 50, and the desired final concentration.

The sulfonic acid in oil utilized may be derived from petroleum oil. The oil used in the process can be any suitably refined crude distillate. An example of a suitable feedstock is a vacuum distillate of appropriate molecular weight that has been refined by solvent extraction and/or hydrotreating to reduce the polynuclear aromatics content. The sulfonic acid solution used in the process is created by reacting the refined crude distillate with fuming sulfuric acid (about 27%–about 33% $SO_3$; oleum) or gaseous $SO_3$. When the feedstock is contacted with fuming sulfuric acid, mono-aromatics are converted into mono-sulfonic acid and the residual poly-nuclear aromatics are converted into polysulfonic acid. The polysulfonic acid plus $SO_3$ depleted sulfuric acid form a sludge. This reaction mixture is suitably diluted with about 1 to about 20 volumes of a miscible solvent to reduce viscosity, and the sludge is separated out by gravity settling, leaving the sulfonic acid in a solvent/oil solution. Dissolved or entrained $SO_3$ and/or $SO_2$, produced as a byproduct of side reactions between the oil and the $SO_3$, are removed from the solution if present. One method of removal is stripping with nitrogen or another inert gas. The solution can also be centrifuged to remove traces of sludge prior to removal of dissolved or entrained $SO_2$ or $SO_3$.

Suitable solvents include any $C_3$ to $C_{10}$ alkane, toluene or any low viscosity, miscible solvent. Most preferred is heptane or commercially available mixtures of heptane isomers.

To the cleaned sulfonic acid/solvent/oil solution is added about 1 mol per mol to about 5 mol per mol sulfonic acid of water and about 1 mol per mol to about 10 mol per mol sulfonic acid of calcium hydroxide to form the reaction mixture.

The reaction mixture is heated with mixing such as stirring to a temperature of from about 40° C. to about 200° C., preferably from about 80° C. to about 120° C. The mixture is preferably stirred for a period of time up to about 60 minutes, more preferably up to about 30 minutes.

The resulting mixture is then separated to remove excess calcium hydroxide and optionally if present, salts formed from residual sludge or $SO_2$. One method of separating the mixture is centrifugation. Centrifugation should be performed for a sufficient amount of time to remove the excess calcium hydroxide and any salts. This period of time can be any such sufficient amount of time, for example, 20 minutes. The presence of the solvent greatly improves the speed of separation. The solvent is recovered from the clear centrate for recycle by any convenient means such as a solvent stripper. The product may be further concentrated via distillation or vacuum flashing to remove a portion or all of the unreacted oil. The recovered essentially chloride free calcium sulfonate product can be in various amounts of oil depending on the degree of concentration when the oil is removed. The calcium sulfonate product in oil preferably has a viscosity of between 10 cSt/100° C. and 100 cSt/100° C. It is preferable to remove the dissolved or entrained $SO_2$ or $SO_3$ if present from the sulfonic acid solution to obtain such viscosity. The essentially chloride free calcium sulfonate in oil can be recovered from the solvent removal step or after concentrating by removing at least a portion of the oil or from both, for example, by collecting the essentially chloride free calcium sulfonate in oil at suitable steps in the process such as after the solvent removal step.

In one embodiment of the process of the invention, such process may be operated in a continuous fashion in a manner such as that shown in FIG. 1. Sulfonic acid 1 is added to a reactor 7, followed by water 3 and lime 5. The resultant mixture then undergoes separation 9, with the lime and water being removed. The next step is solvent recovery 11, followed by concentration 13 to produce the calcium sulfonate in base oil 15.

The following examples are meant to further illustrate the invention without limiting its scope.

COMPARATIVE EXAMPLES

Set I

A sulfonic acid solution (75 g) containing a mixture of petroleum sulfonic acid (8 wt %, average molecular weight of about 440 g/mol), commercial heptanes (60 wt %), and lubricating oil (32 wt %) was used in the following examples. This mixture was further treated by centrifugation and nitrogen stripping before being used in the examples.

Water, calcium hydroxide and tertiary butyl alcohol (TBA), as a promoter, were added to 75 g of sulfonic acid. The resulting reaction mixture was heated with stirring for a specified time in an Erlenmeyer flask equipped with a reflux condenser. For temperatures above the boiling point of the mixture, a stainless steel reaction vessel was used to contain the mixture under pressure. After stirring, the mixture was transferred to a centrifuge tube and centrifuged for 10–20 minutes. Table I shows the resulting Strong Base Number (SBNC, measured according to ASTM D974) of the centrate for various values of pretreatment, TBA content, water content, lime content, reaction time, reaction temperature, and centrifugation time.

TABLE I

COMPARATIVE EXAMPLES SET I - WITH PRETREATMENT AND WITH TBA

| Comp. Example | TBA, mol/mol sulfonic acid | Water, mol/mol sulfonic acid | Lime, mol/mol sulfonic acid | Reaction Temp. ° C. | Reaction time, min | Centrifugal time, min | Centrate SBNC, mg KOH/g |
|---|---|---|---|---|---|---|---|
| 1 | 2.1 | 2.4 | 4.0 | 80 | 10 | 10 | 2.2 |
| 2 | 2.1 | 2.4 | 4.0 | 82 | 30 | 10 | 2.3 |
| 3 | 1.0 | 1.7 | 4.0 | 140 | 30 | 10 | 2.9 |
| 4 | 1.2 | 1.9 | 4.0 | 140 | 30 | 10 | 3.2 |

TABLE I-continued

COMPARATIVE EXAMPLES SET I - WITH PRETREATMENT AND WITH TBA

| Comp. Example | TBA, mol/mol sulfonic acid | Water, mol/mol sulfonic acid | Lime, mol/mol sulfonic acid | Reaction Temp. ° C. | Reaction time, min | Centrifugal time, min | Centrate SBNC, mg KOH/g |
|---|---|---|---|---|---|---|---|
| 5 | 1.2 | 1.7 | 4.0 | 140 | 30 | 10 | 3.0 |
| 6 | 1.2 | 2.7 | 4.0 | 140 | 30 | 10 | 2.9 |

As can be seen, a base number of up to 3.2 can be obtained by optimizing the amount of TBA, water, and temperature.

COMPARATIVE EXAMPLES

Set II

The Comparative Examples in Set II were performed as in Comparative Examples Set I, however, the sulfonic acid was not treated by centrifugation and nitrogen stripping prior to reaction and no TBA was added. The results from these examples are in Table II. Acidic results are shown as a negative SBNC value.

TABLE II

COMPARATIVE EXAMPLES SET II - NO PRETREATMENT, NO TBA

| Comp. Example | Water, mol/mol sulfonic acid | Lime, mol/mol sulfonic acid | Reaction Temp, ° C. | Reaction time, min | Centrifuge time, min | Centrate SBNC, mg KOH/g |
|---|---|---|---|---|---|---|
| 7 | 0.5 | 3.0 | 26 | 10 | 10 | −7.5 |
| 8 | 4.6 | 3.0 | 26 | 10 | 10 | −0.3 |
| 9 | 12.7 | 3.0 | 26 | 10 | 10 | −0.3 |
| 10 | 0.5 | 3.0 | 82 | 10 | 10 | −1.1 |
| 11 | 2.7 | 4.0 | 82 | 30 | 10 | 0.2 |

These Comparative Examples show the results obtained without pretreating the sulfonic acid.

COMPARATIVE EXAMPLES

Set III

The Comparative Examples in Set III were performed as in Comparative Examples Set I, however, the sulfonic acid was not treated by centrifugation and nitrogen stripping prior to reaction. The results from these examples are in Table IV. Acidic results are shown as a negative SBNC value.

These examples show results obtained without pretreating the sulfonic acid, but adding TBA to the reaction mixture. A maximum SBNC value of 2.5 was obtained.

EXAMPLES

A sulfonic acid solution (75 g) containing a mixture of petroleum sulfonic acid (8 wt %, average molecular weight of about 440 g/mol), commercial heptanes (60 wt %), and lubricating oil (32 wt %) was used in the following examples. This mixture was further treated by centrifugation and nitrogen stripping before being used in the examples.

Water and calcium hydroxide were added to 75 g of the treated sulfonic acid solution. The resulting reaction mixture was heated with stirring for the reaction time in an Erlenmeyer flask equipped with a reflux condenser. For temperatures above 82° C., a stainless steel reaction vessel was used to contain the mixture under pressure. After stirring, the mixture was transferred to a centrifuge tube and centrifuged for 10–20 minutes. Table IV shows the resulting Strong Base Number (SBNC, measured according to ASTM D974) of the centrate for various values of water content measured in mol/mol of sulfonic acid, lime content measured in mol/mol of sulfonic acid, reaction temperature measured in ° C., and reaction time and centrifugation time measured in minutes.

TABLE III

COMPARATIVE EXAMPLES SET III - NO PRETREATMENT, WITH TBA

| Comp. Example | TBA, mol/mol sulfonic acid | Water, mol/mol sulfonic acid | Lime, mol/mol sulfonic acid | Reaction Temp. ° C. | Reaction time, min | Centrifuge time, min | Centrate SBNC, mg KOH/g |
|---|---|---|---|---|---|---|---|
| 12 | 10.9 | 0.5 | 3.0 | 26 | 10 | 10 | −7.0 |
| 13 | 1.4 | 5.7 | 3.0 | 26 | 10 | 10 | 1.0 |
| 14 | 3.3 | 3.3 | 4.0 | 26 | 20 | 20 | 0.8 |
| 15 | 7.5 | 6.3 | 3.0 | 26 | 10 | 10 | 0.8 |
| 16 | 7.9 | 3.1 | 3.0 | 26 | 10 | 10 | −0.3 |
| 17 | 4.5 | 5.0 | 3.0 | 26 | 10 | 10 | 1.9 |
| 18 | 4.6 | 4.1 | 3.0 | 60 | 10 | 10 | 2.3 |
| 19 | 4.2 | 3.9 | 4.0 | 60 | 20 | 20 | 2.5 |
| 20 | 2.1 | 2.1 | 3.0 | 82 | 10 | 10 | 2.4 |

Figure 2:
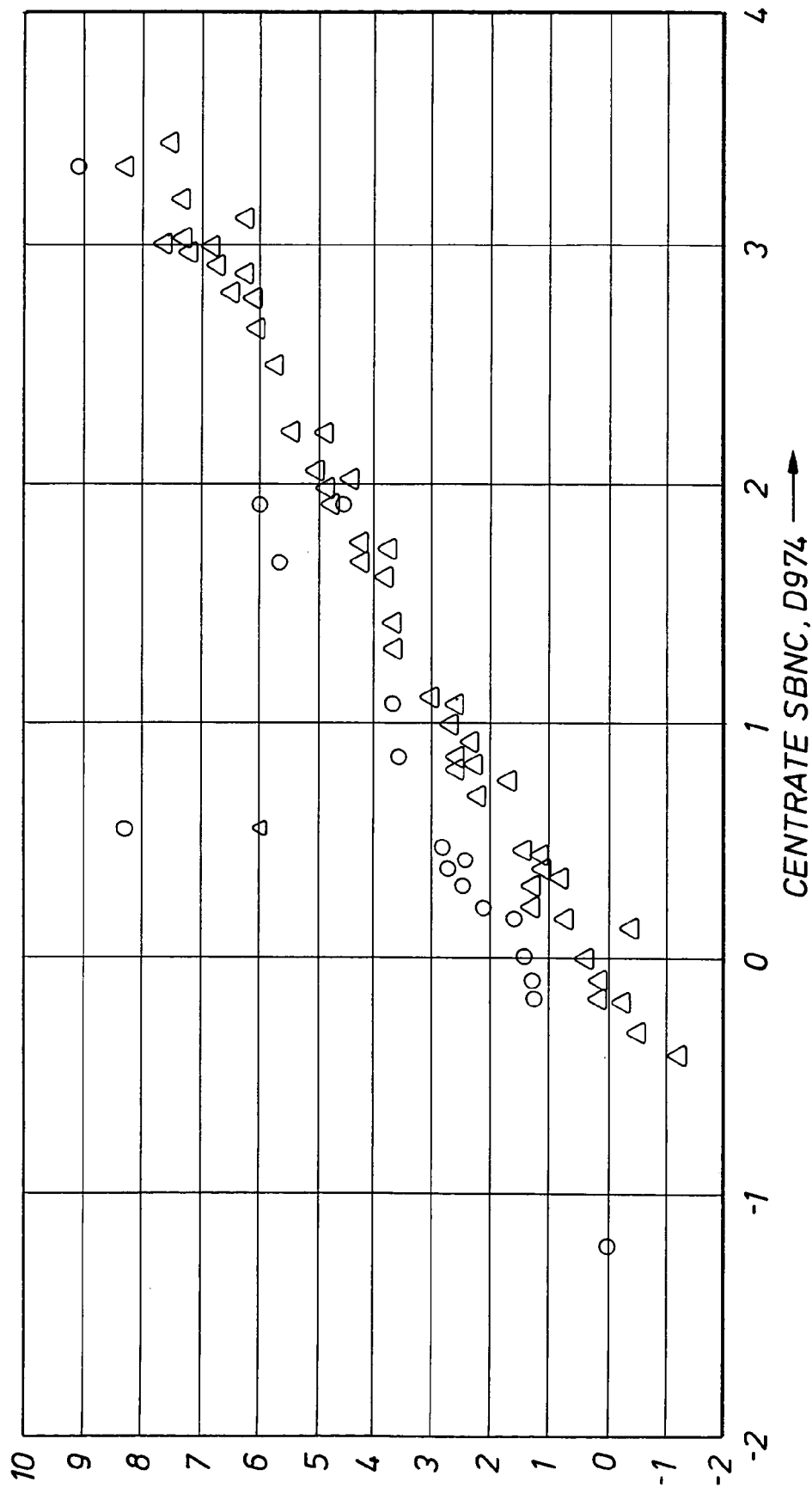
FIG. 2—This figure shows the relationship between the Strong Base Number (SBNC) of the calcium sulfonate solution produced by the invention and the SBNC of the product after solvent stripping.

FIG. 2 shows the correlation between the SBNC of the centrate and the concentrated product.

TABLE IV

EXAMPLES

| Example | Water, mol/mol sulfonic acid | Lime, mol/mol sulfonic acid | Reaction Temp, °C. | Reaction time, min | Centrifuge time, min | Centrate SBNC, mg KOH/g |
|---|---|---|---|---|---|---|
| 1 | 2.3 | 4.0 | 60 | 30 | 10 | 0.4 |
| 2 | 2.7 | 4.0 | 60 | 30 | 10 | 2.7 |
| 3 | 3.1 | 4.0 | 60 | 30 | 10 | 2.3 |
| 4 | 3.5 | 4.0 | 60 | 30 | 10 | 2.1 |
| 5 | 2.4 | 4.0 | 82 | 10 | 10 | 0.9 |
| 6 | 2.4 | 4.0 | 82 | 30 | 10 | 2.2 |
| 7 | 2.8 | 4.0 | 82 | 30 | 10 | 3.3 |
| 8 | 1.5 | 4.0 | 117 | 30 | 10 | 3.5 |
| 9 | 1.7 | 4.0 | 117 | 30 | 10 | 3.6 |
| 10 | 1.9 | 4.0 | 117 | 30 | 10 | 3.3 |
| 11 | 2.2 | 1.0 | 117 | 30 | 10 | 0.7 |
| 12 | 2.6 | 1.0 | 117 | 30 | 10 | 2.5 |
| 13 | 3.0 | 1.0 | 117 | 30 | 10 | 2.3 |
| 14 | 2.2 | 4.0 | 140 | 1 | 10 | 3.4 |
| 15 | 2.2 | 4.0 | 140 | 10 | 10 | 3.5 |
| 16 | 1.3 | 4.0 | 140 | 30 | 10 | 0.5 |
| 17 | 1.9 | 4.0 | 140 | 30 | 10 | 3.5 |
| 18 | 2.0 | 4.0 | 140 | 30 | 10 | 3.6 |
| 19 | 2.2 | 4.0 | 140 | 30 | 10 | 3.5 |
| 20 | 3.1 | 4.0 | 140 | 30 | 10 | 2.8 |

These examples show that a base number of 3.6 can be achieved with the method of the invention. Table V and corresponding FIG. 2 show the relationship between the centrate SBNC and the stripped centrate (i.e., after solvent removal) SBNC and TBN such that a value for the stripped product can be extrapolated from FIG. 2.

TABLE V

RELATIONSHIP BETWEEN CENTRATE SBNC AND STRIPPED CENTRATE SBNC AND TBN

| Example | Centrate SBNC ASTM D974 | Stripped Centrate SBNC ASTM D974 | Stripped Centrate TBN ASTM D2896 |
|---|---|---|---|
| 1 | −1.23 | −2.47 | 0.00 |
| 2 | −0.18 | 0.21 | 1.24 |
| 3 | −0.10 | 0.17 | 1.28 |
| 4 | 0.00 | 0.40 | 1.40 |
| 5 | 0.16 | 0.75 | 1.56 |
| 6 | 0.21 | 1.33 | 2.12 |
| 7 | 0.30 | 1.32 | 2.48 |
| 8 | 0.37 | 1.10 | 2.72 |
| 9 | 0.41 | 1.18 | 2.44 |
| 10 | 0.46 | 1.44 | 2.85 |
| 11 | 0.85 | 2.61 | 3.56 |
| 12 | 1.07 | 2.66 | 3.69 |
| 13 | 1.67 | 4.29 | 5.67 |
| 14 | 1.91 | 4.70 | 6.00 |
| 15 | 3.35 | 8.36 | 9.16 |

Figure 3:
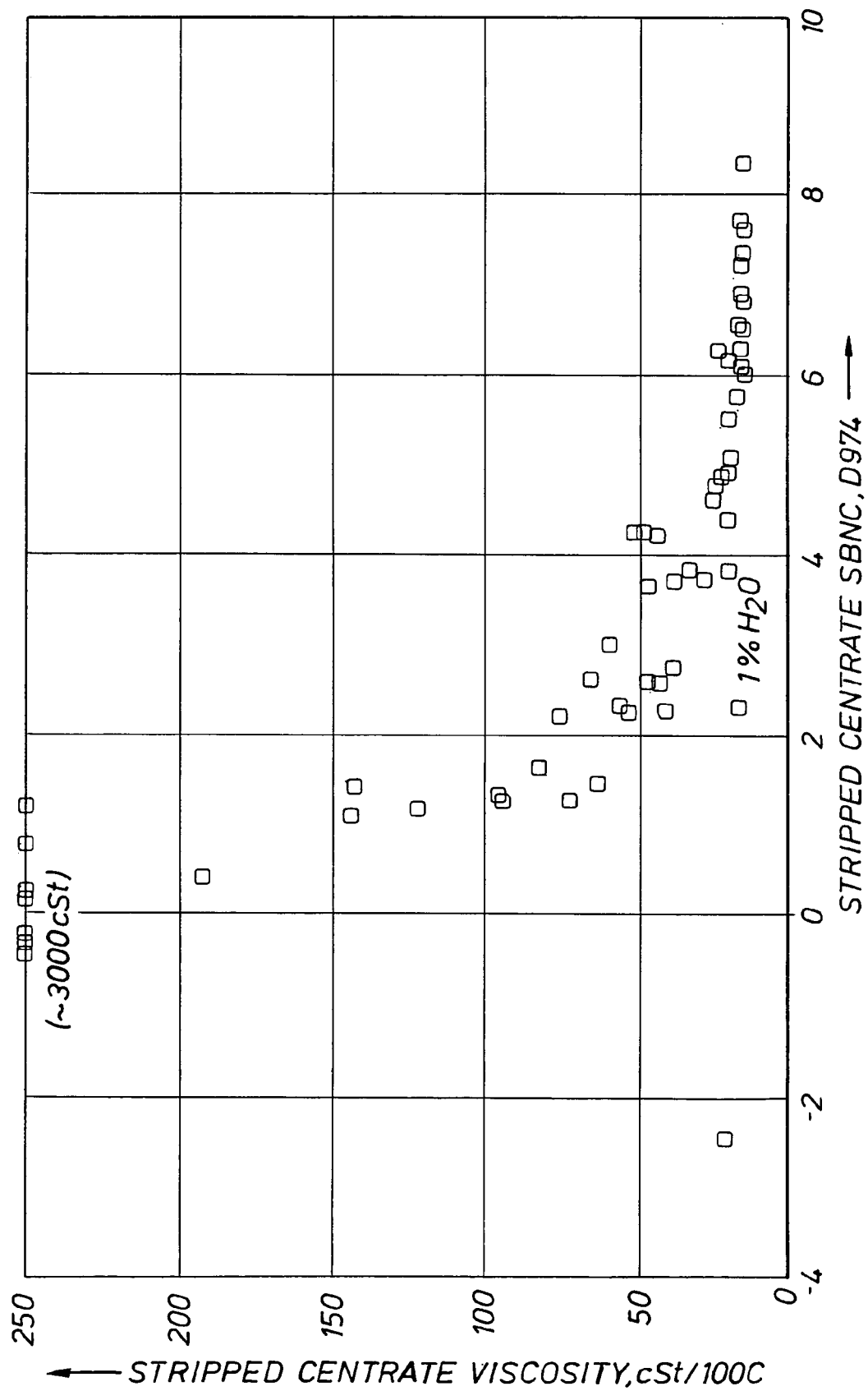
FIG. 3—This figure shows the relationship between product viscosity and the SBNC of the product after solvent stripping.

In order to improve the product viscosity, it is advantageous to produce a higher base number product while still maintaining the product in the low base number product range. From FIG. 2, it can be seen that a base number of 3.6 correlates to a stripped centrate SBNC of about 9.1. FIG. 3 shows the relationship between the base number of the stripped product of the invention and the viscosity of the product. From Table VI and FIG. 3 it can be seen that a viscosity of about 15 cSt at 100° C. correlates to a stripped centrate SBNC of about 9.1.

TABLE VI

Relationship between SBNC of Stripped Product and Viscosity of Stripped Product

| Example | Stripped Centrate SBNC ASTM D974 | Stripped Centrate Viscosity/100° C. ASTM D445 |
|---|---|---|
| 1 | −2.47 | 22 |
| 2 | −1.17 | 250 |
| 3 | 0.00 | 3000 |
| 4 | 0.50 | 191 |
| 5 | 1.00 | 121 |
| 6 | 1.68 | 82.2 |
| 7 | 2.64 | 47.1 |
| 8 | 4.59 | 25.5 |
| 9 | 6.08 | 15.9 |
| 10 | 7.27 | 15.6 |
| 11 | 8.36 | 14.8 |

We claim:

1. A process for the production of low base number calcium sulfonates comprising:
    a. preparing a sulfonic acid-oil solution by adding about 1 to about 20 volumes of a miscible solvent to a sulfonic acid-oil feedstock, centrifuging said solution and removing dissolved or entrained $SO_2$ or $SO_3$ via stripping if present;
    b. mixing the sulfonic acid-oil solution with about 1 to about 5 moles of water per mol of sulfonic acid and about 1 to about 10 moles of calcium hydroxide per mole of sulfonic acid to provide a reaction mixture;
    c. heating the reaction mixture to a temperature in the range of about 40° C. to about 200° C.;
    d. separating excess calcium hydroxide from the heated-reaction mixture to produce a reaction product comprising solvent, oil, and calcium sulfonate;
    e. removing the solvent from the reaction product to produce an intermediate product comprising oil and calcium sulfonate;

f. optionally concentrating the intermediate product by removing at least a portion of the oil to produce a concentrated product; and g. recovering the intermediate product and/or concentrated product, wherein the product is essentially chloride free calcium sulfonate in oil.

2. The process of claim 1 in which the solvent is heptane.

3. The process of claim 1 in which the dissolved or entrained $SO_2$ or $SO_3$ is removed via stripping with nitrogen.

4. The process of claim 1 in which the amount of water is from about 1 to about 3 mol/mol of sulfonic acid.

5. The process of claim 1 in which the amount of calcium hydroxide is about 1 to about 5 mol/mol of sulfonic acid.

6. The process of claim 1 in which reaction mixture is heated at a temperature in the range from about 80° C. to about 140° C.

7. The process of claim 1 in which the reaction mixture is mixed for a period of time up to 60 minutes.

8. The process of claim 1 in which the reaction mixture is mixed for a period of time up to 30 minutes.

9. The process of claim 1 in which excess calcium hydroxide is separated from the reaction mixture by centrifugation.

10. The process of claim 9 in which the centrifugation is performed for less than about 20 minutes.

11. The process of claim 1 in which the intermediate product is concentrated by a method selected from the group consisting of distillation and vacuum flashing.

12. The process of claim 1 in which the process is a continuous process.

13. The process of claim 1 in which the solvent is heptane, the dissolved or entrained $SO_2$ or $SO_3$ is removed via stripping with nitrogen, and the intermediate product is concentrated by a method selected from the group consisting of distillation and vacuum flashing.

14. The process of claim 13 in which the process is a continuous process.

15. The process of claim 13 in which the centrifugation to remove excess calcium hydroxide is performed for less than about 20 minutes.

16. The process of claim 13 in which the calcium sulfonate in oil has a viscosity of between about 10 cSt/100° C. and about 100 cSt/100° C.

17. The process of claim 16 in which the process is a continuous process.

18. The process of claim 17 in which the product is further concentrated by distillation.

19. A process for the production of low base number calcium sulfonate comprising:

a. preparing a sulfonic acid solution in oil by adding about 1 to about 20 volumes of a miscible solvent to sulfonic acid and removing dissolved or entrained $SO_2$ or $SO_3$ if present;

b. mixing the sulfonic acid solution in oil with about 1 to about 5 moles of water per mol of sulfonic acid and about 1 to about 10 moles of calcium hydroxide per mole of sulfonic acid to produce a reaction mixture;

c. heating the reaction mixture with stirring to a temperature between about 40° C. and about 200° C.;

d. separating excess calcium hydroxide from the heated-reaction mixture; and e. recovering the essentially chloride free calcium sulfonate product from the separated-reaction mixture by removing the solvent, wherein the product after solvent removal is further concentrated by removing at least a portion of the oil.

20. The process of claim 19 in which the oil is removed by a method selected from the group consisting of distillation and vacuum flashing.

21. The process of claim 19 in which the dissolved or entrained $SO_2$ or $SO_3$ is removed via stripping with nitrogen.

22. The process of claim 21 in which the sulfonic acid is centrifuged prior to stripping.

23. The process of claim 19 in which the amount of water is from about 1 to about 3 mol/mol of sulfonic acid.

24. The process of claim 19 in which the amount of calcium hydroxide is about 1 to about 5 mol/mol of sulfonic acid.

25. The process of claim 19 in which reaction mixture is heated at a temperature in the range from about 80° C. to about 140° C.

26. The process of claim 19 in which the reaction mixture is mixed for a period of time up to 60 minutes.

27. The process of claim 19 in which the reaction mixture is mixed for a period of time up to 30 minutes.

* * * * *